United States Patent
Kuzmanovic

(10) Patent No.: US 7,344,305 B2
(45) Date of Patent: Mar. 18, 2008

(54) REMOTE VISUAL FEEDBACK OF COLLIMATED AREA AND SNAPSHOT OF EXPOSED PATIENT AREA

(75) Inventor: Miljan Kuzmanovic, Mount Prospect, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 11/558,965

(22) Filed: Nov. 13, 2006

(65) Prior Publication Data

US 2008/0037708 A1 Feb. 14, 2008

Related U.S. Application Data

(60) Provisional application No. 60/834,680, filed on Aug. 1, 2006.

(51) Int. Cl.
*A61B 6/08* (2006.01)
(52) U.S. Cl. ...................................... 378/206; 378/205
(58) Field of Classification Search ........ 378/205–207, 378/147–148
See application file for complete search history.

(56) References Cited

U.S. PATENT DOCUMENTS

| 4,203,037 | A | 5/1980 | Gur et al. |
| 4,229,656 | A | 10/1980 | Iversen et al. |
| 4,502,147 | A | 2/1985 | Michaels |
| 6,106,152 | A | 8/2000 | Thunberg |
| 6,377,656 | B1 | 4/2002 | Ueki et al. |
| 6,614,877 | B2 | 9/2003 | Anderton |
| 6,711,433 | B1 * | 3/2004 | Geiger et al. ............... 600/431 |
| 6,779,920 | B2 | 8/2004 | Stevanovic et al. |
| 7,010,091 | B2 * | 3/2006 | Hayashida et al. ........ 378/98.8 |
| 7,116,752 | B2 | 10/2006 | Takahashi et al. |
| 2003/0223540 | A1 * | 12/2003 | Hayashida et al. ........ 378/98.8 |

* cited by examiner

*Primary Examiner*—Hoon Song

(57) ABSTRACT

A method and system are providing for performing X-ray diagnostic imaging using a camera image controlled to image a field of view (FOV) that is substantially coincident and coplanar with a radiation footprint or FOV of an X-ray beam radiated towards a patient under examination. Both the X-ray beam and camera FOVs are shaped and/or limited by collimation. The method and system include acquiring a camera image with a collimated FOV to an X-ray beam FOV before X-ray imaging a patient, displaying the camera image and adjusting the collimation and patient positioning to define the X-ray beam FOV based on the displayed camera image before X-ray imaging the patient. After adjustment, the method and system include radiating the X-ray beam as collimated during the patient X-ray imaging, acquiring and processing captured X-ray image information to reconstruct an X-ray image and displaying the reconstructed X-ray image with the displayed camera image. The step of radiating may be postponed or interrupted for X-ray beam readjustment or patient repositioning for desired X-ray imaging based on the camera image displayed.

43 Claims, 5 Drawing Sheets

REMOTE VISUAL FEEDBACK OF COLLIMATED AREA AND SNAPSHOT OF EXPOSED PATIENT AREA

PRIORITY CLAIM TO RELATED APPLICATION

This application claims priority from U.S. Provisional Patent Application Ser. No. 60/834,680, filed Aug. 1, 2006, the disclosure of which is incorporated by reference in its entirety herein.

BACKGROUND OF THE INVENTION

1. Field of the Invention

The present invention relates to medical X-ray imaging, and more particularly the present invention relates to an X-ray system that includes a camera to provide visual feedback to an operator of the system during pre-examination testing and adjustment, including a snapshot of a collimator-shaped patient FOV. In an embodiment, a camera image is provided by the camera to the X-ray system, and a feedback signal is generated in response to the camera image to support collimator and/or X-ray tube adjustment, patient positioning and movement, etc.

2. Description of the Related Art

X-ray imaging systems for digital radiography are used for conventional imaging of anatomical background including solid structures, soft tissue such as in cardiac vascular imaging using such techniques including without limitation digital spot imaging, digital subtraction angiography (DSA) and live fluoroscopy roadmapping. X-ray imaging systems include an X-ray source and X-ray capture device such as image intensifying screen, or digital flat panel detector to convert the X-ray energy defining the radiation image into light. X-ray systems also include various mechanisms for preventing direct exposure from the X-ray beam, scattered X-rays from reaching the detector or image intensifier and other beam-shaping mechanisms including X-ray collimators or beam-limiting devices. X-ray collimators adjust the X-ray beam to an extent necessary for imaging patient anatomy within desired fields of view (FOV). For example, a collimator may be adjusted during the examination for each image taken to optimally cover the part of the image in which no body part, or non-relevant body parts are located, i.e., outside the FOV.

X-ray imaging systems may include various displays, panels, consoles, workstations, etc., with user interfaces such as keyboards, switches, dials, trackballs, joysticks, etc., that enable an operator to view an image and make adjustments for further imaging. Input devices control operations such as the image contrast, brightness, image blur and noise in the produced image. For that matter, because manually setting the collimator parameters, such as at each station in an angiographic study of leg vasculature for a mask run, and saving the settings is cumbersome and time consuming, automatic collimator adjustment functions have been developed. U.S. Pat. No. 6,055,295, commonly owned, discloses a system and method for automatically setting the collimator of an X-ray imaging system at the time of image acquisition.

U.S. Pat. No. 6,106,152, commonly owned, discloses an X-ray imaging system with an X-ray source, X-ray tube and collimator to limit, adjust or shape the radiated X-ray beam. During operation, a test exposure is acquired with the disclosed system and used to adjust the collimator to position the X-ray beam in relation to a digital detector, such as a flat panel detector, focusing the patient FOV. In this way, images may be acquired and processed for desired views.

The image processing typically includes adjusting contrast and background removal for desirable imaging quality. But collimator adjusting or adjusting proper distances between the patient and X-ray source may be insufficient nevertheless where the patient or table has moved after set-up. This is particularly so with spot imaging, and techniques where a patient is physically adjusted, and the system parameters physically adjusted, and there is a time lag before the intended examination procedure. Required readjustment of a patient who has moved between system physical adjustment and diagnostic or interventional imaging causes double work, in which the clinician is required to reposition the patient, and possibly recalibrate. Patient movement may be acute where a patient is unconscious, for example, during an emergency intervention, and may move involuntarily.

Where readjustment is required after setup and test imaging, the patient, and possibly the clinician are exposed to unnecessary radiation where the test imaging must be repeated, or the examination is inadvertently conducted with an improper FOV. Again there is a cost in patient throughput time, clinician time and energy, and cost. In addition, where a clinician may wish an alternative X-ray image based on a first image, or a series of images of a fixed patient FOV, repositioning is complicated if the patient has moved without the clinician realizing it until the "next" image is viewed.

It would be well-received, therefore, to the skilled artisan and clinicians alike, to have use of a system and method that overcomes the shortcomings of the prior art, that allows the clinician to be readily sure that the FOV is as arranged prior to test imaging and diagnostic imaging, particularly in cases where the imaging position is modified for particular studies.

SUMMARY OF THE INVENTION

To that end, aspects of the invention comprise an X-ray examination system that includes a camera proximate an X-ray source or tube so that the camera may image substantially the same FOV as the actual X-ray radiation pattern footprint or FOV in the patient's fixed examination position. By viewing the camera image, the operator or clinician may determine directly, particularly during pre-examination adjusting of both the patient and system elements, that the proper FOV will be irradiated. That is, the camera provides a view of the FOV or radiation pattern footprint at the patient, wherein the viewer immediately knows if it has changed, or needs to be changed by patient readjustment, collimator readjustment, etc. The method of examination in accordance with an embodiment of the invention is different from conventional adjustment or test imaging, and diagnostic imaging methods. By use of the inventive system and method, the clinician may realize improved patient throughput, reduced patient and/or clinician exposure to unnecessary X-ray exposure, unnecessary discarded images and reduced dose levels overall due to improved collimator adjustment.

In one embodiment, the inventive X-ray diagnostic imaging system includes an X-ray source for generating and controlling an X-ray beam radiated towards a patient under examination. The X-ray source includes an X-ray tube, an X-ray collimator assembly and a camera disposed with respect to the X-ray tube. The camera may be arranged to move with the X-ray tube to image with an adjustable field of view (FOV) at a physical position of the X-ray beam at the patient's body that is substantially coincident with and at least as large as a maximum radiation-pattern footprint or FOV of the radiated X-ray beam. Both the radiated beam footprint and camera FOV are shaped and/or limited by collimator assembly operation. The system includes in addition an X-ray imaging device arranged for receiving the X-ray beam after it has passed through the patient and acquiring latent image frames of a region of interest (ROI) within the patient's anatomy. A system controller coupled to the X-ray source and X-ray imaging device controls latent image frame acquisition and post-acquisition processing, including controlling the X-ray tube, X-ray collimator assembly, camera and X-ray imaging device positioning.

An image processing chain comprising an image processor that is coupled to the system controller receives the latent image frames from the X-ray imaging device for processing and a display device coupled to the image processing chain displays post-processed image frames as an X-ray diagnostic image of the ROI. A feedback signal is generated in response to an image signal acquired by the camera. The feedback signal is provided by the system to control the collimator assembly and the position of the X-ray tube and X-ray imaging device. The X-ray diagnostic imaging system provides that the position of the camera and the X-ray tube is synchronized when a beam-limiting means comprising the collimator assembly forms an opening for passing the shaped beam that is at a maximum. The feedback signal may be utilized by the X-ray diagnostic imaging system for automatic synchronization, or the feedback signal is provided by a user based on the user's observation of the FOV depicted by the camera image.

The camera image may be displayed with the X-ray image on the display device during normal imaging operation, but it is preferable to acquire camera images only when the X-ray system is in a pretest or physical set-up operation, wherein a size of the collimator opening is arranged to constrict the FOV of the X-ray beam and camera substantially similarly. The camera may include a conventional light that lights the camera FOV; it is preferable that the camera is a video camera, and most preferably that the video camera is miniaturized. Of course, a focusing system that is included with the camera to focus the camera FOV must be disposed outside a maximum cross-section area of the X-ray beam at maximum beam width.

DESCRIPTION OF DRAWING FIGURES

An understanding of the present invention can be gained from the following detailed description of embodiments of the invention, taken in conjunction with the accompanying drawings of which:

DETAILED DESCRIPTION OF EXEMPLARY EMBODIMENTS

Figure 1A:
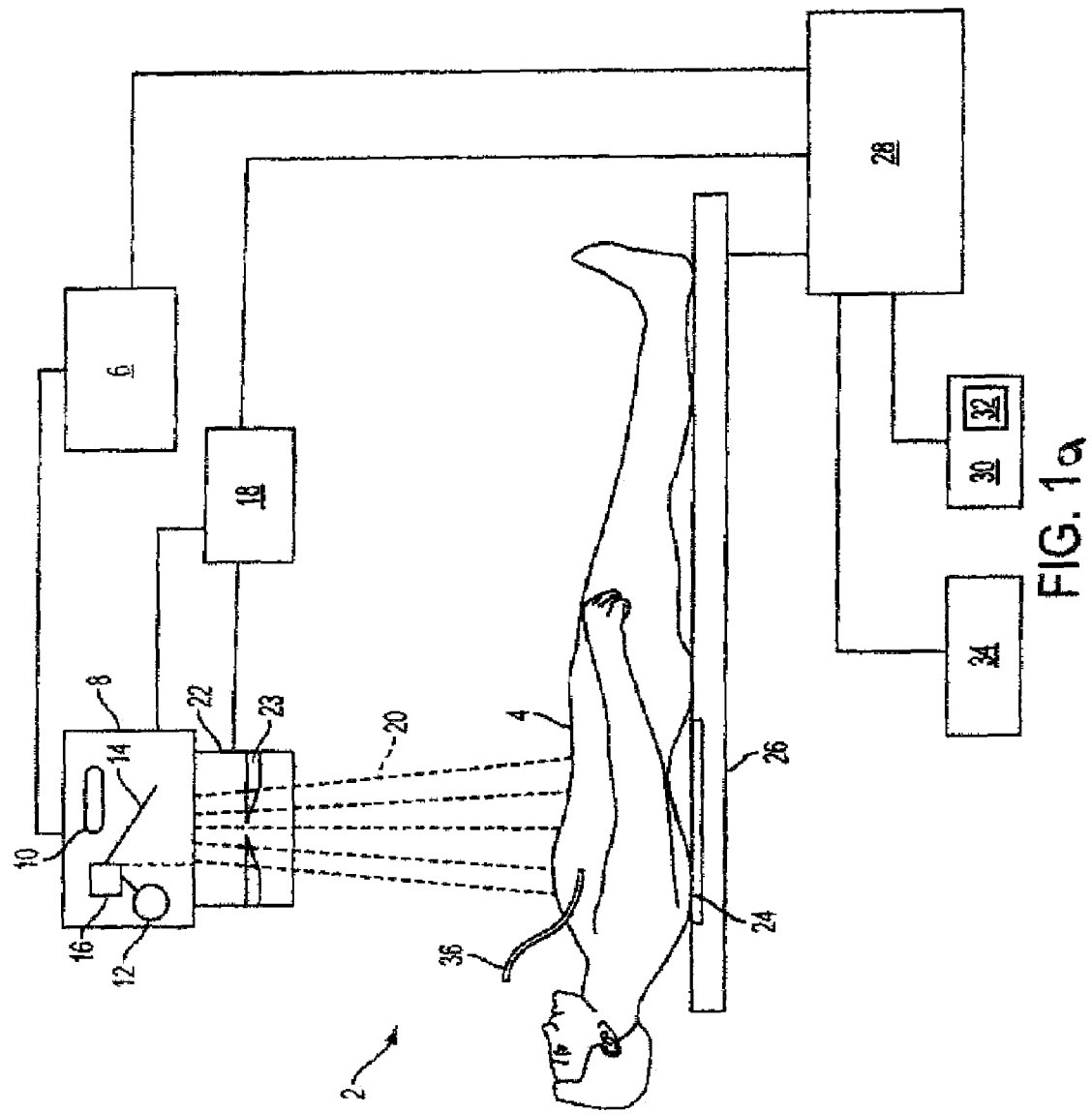
FIG. 1a is a schematic representation of an X-ray diagnostic imaging system and camera of the invention.

Reference will now be made in detail to exemplary embodiments of the present invention, examples of which are illustrated in the accompanying drawings, wherein like reference numerals refer to like elements throughout.

FIG. 1a represents an X-ray diagnostic imaging system 2 of the invention, under which is a patient 4 undergoing an X-ray examination procedure. The X-ray system 2 includes a high voltage transformer assembly 6, an X-ray source housing 8, comprising an X-ray tube 10, a camera 12, mirror 14 and mirror drive device 16. The X-ray source housing 8 is attached to a collimator assembly 22, including beam-limiting filter plates 23. The mirror drive device controls the positioning of mirror 14 into and out of the path of an X-ray beam 20, from X-ray tube 10, controls camera positioning and operation, and exchanges mirror position and camera position information with the system through position detecting and control device 18. With respect to the camera and mirror, mirror drive device 16 moves the mirror 14 and/or camera 12, and controls camera image acquisition. The position detecting control device 18 provides the camera with a feedback control signal to adjust the mirror placement and focus the camera to capture a field of view (FOV) at the patient.

Figure 1B:
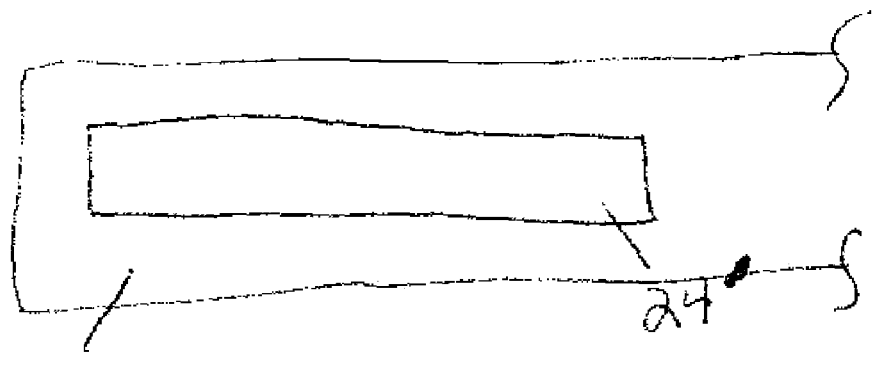
FIG. 1b is a schematic representation of an X-ray detection device of the invention embodied as an image intensifier assembly.
Figure 1C:
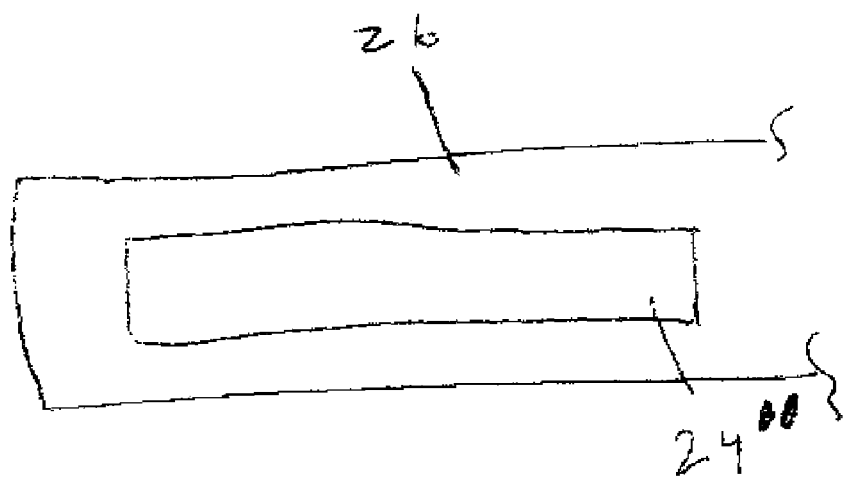
FIG. 1c is a schematic representation of an X-ray detection device of the invention embodied as an image intensifier assembly.

The X-ray tube 10 emits X-ray beam 20 during a diagnostic or interventional procedure that is limited and shaped by operation of the collimator assembly 22 before the beam passes through patient 4 and strikes an X-ray detector 24. X-ray detector 24 may be set in a patient table 26, as shown, but is not limited to such an arrangement. The X-ray detector position may vary with the particular X-ray system design as long as the X-ray beam as shaped and adjusted by the collimator assembly 22 strikes it for proper image data acquisition. That is, the exemplary embodiment shown is for explanation purposes to convey the broad inventive concept, and should not be used to limit the scope of the invention to the particular X-ray system shown. For that matter, while detector 8 is depicted as a digital flat panel detector, the invention may be implemented with any detector, such as an image intensifier and associated processing means, or still film cartridge known to the skilled artisan for capturing an X-ray beam and acquire image data. FIG. 1b is a schematic representation of an X-ray detection device of the invention embodied as an image intensifier assembly, shown coextensive with a partial cutaway view of table 26. FIG. 1c is a schematic representation of an X-ray detection device of the invention embodied as an image intensifier assembly, shown coextensive with a partial cutaway view of table 26.

Detector 24 provides the image data acquired as an image frame to an image control and processing sub-system 28. The image control and processing sub-system 28 is connected to the high voltage transformer assembly 6 and position detecting and control device 18. The image control and processing sub-system 28 includes the system's various control and processing means, including without limitation a detector interface, a memory, X-ray beam limiting interface, high voltage transformer assembly interface, image processor or CPU, image condition storage means, camera image processor and control interface and a video signal converting means (none of which are shown explicitly). The camera image processor and control interface processes image information from the camera 12, and provides a camera image for system use and/or display. As mentioned, the feedback control signal is used by the camera and position detecting and control device 18 to control camera positioning, focus and camera image acquisition. The image control and processing sub-system 28 also electrically connects to a control console or work station 30, including user input device(s) 32, and to a display or monitor 34. The user input device 32 allows user input to control image acquisition and display processes, camera operation and collimator operation.

The collimator assembly 22 controls an opening formed by beam limiting plates 23 through which the X-ray beam 20 must pass through for beam shaping. Calibration adjustment information is exchanged with the elements comprising the image control and processing sub-system 28, or other known means, to provide the feedback control signal in order to drive the beam-limiting plates 23, and adjust a distance between the X-ray tube 10 and the detector 24, control the camera 12, mirror 14 and the mirror drive assembly 16. Accordingly, the X-ray system 2 controls the field of view (FOV) at the patient as seen by both the camera 12 and a vantage from the X-ray tube 10, to achieve an image with a desired ROI imaged from within the patient's body. The collimation and positional information may be used for various post-acquisition processes. But because the user can always readily view the FOV through the collimator opening, he/she may immediately sense any imaging problems at the FOV, such as patient or table movement.

A common application of X-ray systems such as inventive X-ray system 2 is monitoring a location of a catheter 36 inside the patient 4. Such catheters may be used for balloon angioplasty, laser ablation, or like procedures, now often used in place of traditional invasive surgery. While FIG. 1a shows the catheter 36 inside patient 4, the X-ray diagnostic imaging system 2 may be used for other purposes, such as guide wire placement, needle placement, tube detection, and non-interventional diagnostic imaging procedures. For a more detailed understanding of using X-ray diagnostic imaging systems for tracking catheters and the like during an interventional procedure, the reader is directed to commonly owned U.S. Pat. No. 5,369,678. U.S. Pat. No. 7,116,752 discusses X-ray beam limiting in detail, including brightness control.

Figure 2:
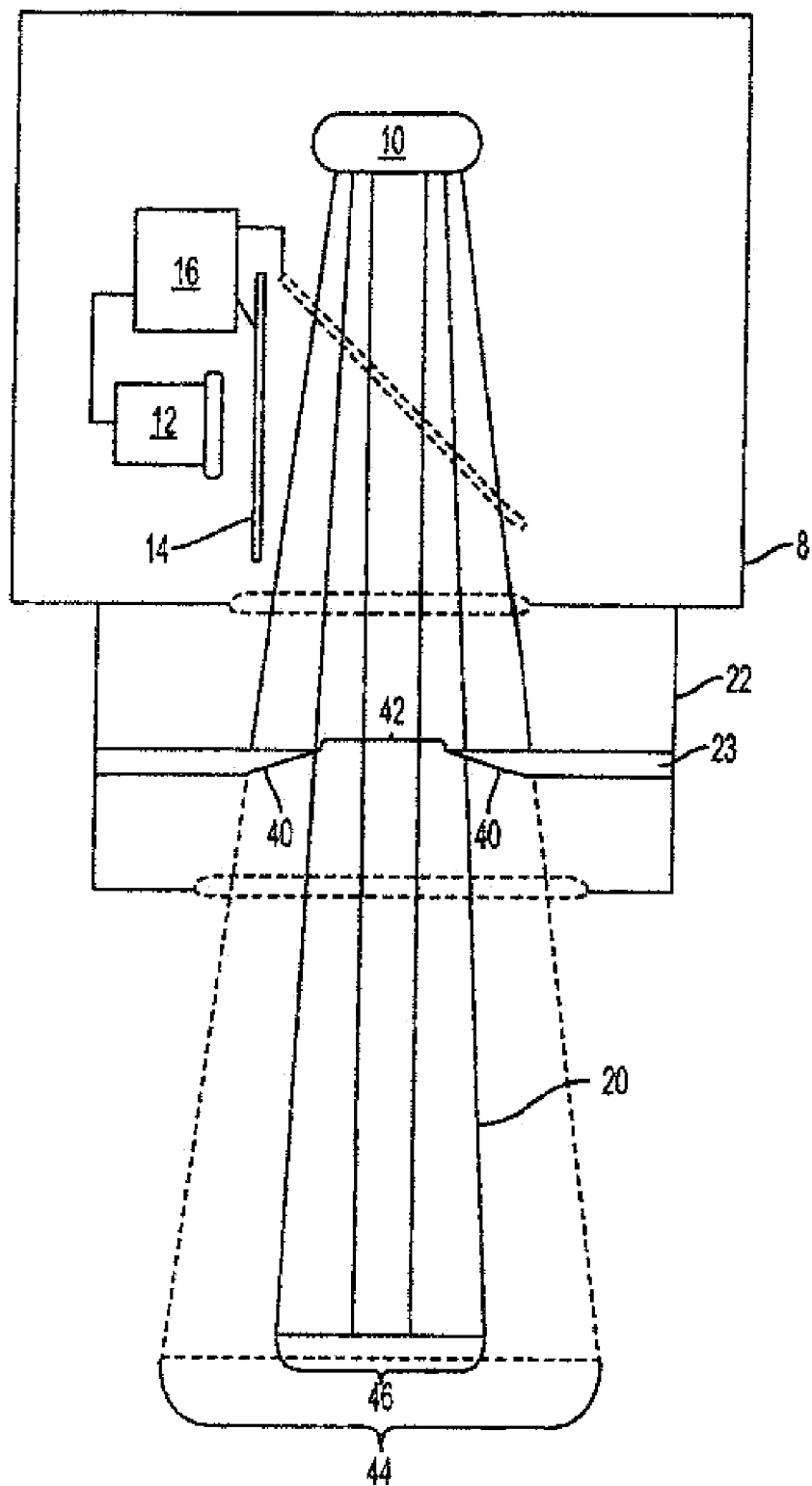
FIG. 2 is schematic diagram of an X-ray source housing that includes a novel camera and focusing assembly, proximate a collimator assembly, of the FIG. 1a X-ray imaging system.

An enlarged view of the X-ray source housing 8, and collimator assembly 22 is shown in FIG. 2. Beam limiting filter plates 23 are shown therein to include a tapered region 40 surrounding a central aperture 42 for shaping X-ray beam 20 and passing the shaped beam into the patient 4. Although one aperture 42 is shown in FIG. 2, a plurality of apertures may be formed in a close pattern so that the X-ray radiation passing through each of the apertures will overlap in a substantially common region. More, the thickness of the filter plates 23 is constructed to change from a maximum value distal from the central aperture 42, to a minimum value bordering the aperture in the tapered plate regions 40. The filter plates are typically made of a material that is semi-transparent to the X-ray beam 20. The camera 12 is adjusted to receive light reflected from the FOV by the mirror 14 during pre-examination testing. More particularly, mirror 14 is adjusted into the area within which the pre-collimated X-ray beam 20 will pass while the X-ray tube is inactive by action of the mirror drive assembly 16.

FOV 44 is the FOV of the camera 12 and the maximum beam pattern footprint of FOV of the X-ray beam 20 at the same planar position. FOV 44 represents the collimated FOV of the X-ray beam, which is substantially the same as that of the aperture-constricted FOV of the camera 12. The mirror drive device 16 communicates its positional and camera image to the system, and receives adjustment information by the feedback control signal, while the X-ray tube is not actively radiating. During adjustment or pre-imaging testing, the physical positioning of the X-ray tube and collimator opening are controlled while the clinician views the limited FOV 46 and collimator blade 23 positions. The limited FOV 46 is in a plane coplanar with an upper most portion of the patient's body. In this way, the clinician can readily detect problems before imaging, avoiding unnecessary imaging. The camera image is preferably provided to the clinician whose response is included in the feedback control signal, or may be provided to image chain processing to generate the feedback control signal. The mirror 14 is controlled out of the path of X-ray beam 20 during imaging. The last camera image obtained before examination imaging with the inventive system 2, may be maintained on the display for quick reference during the examination.

Figure 2A:
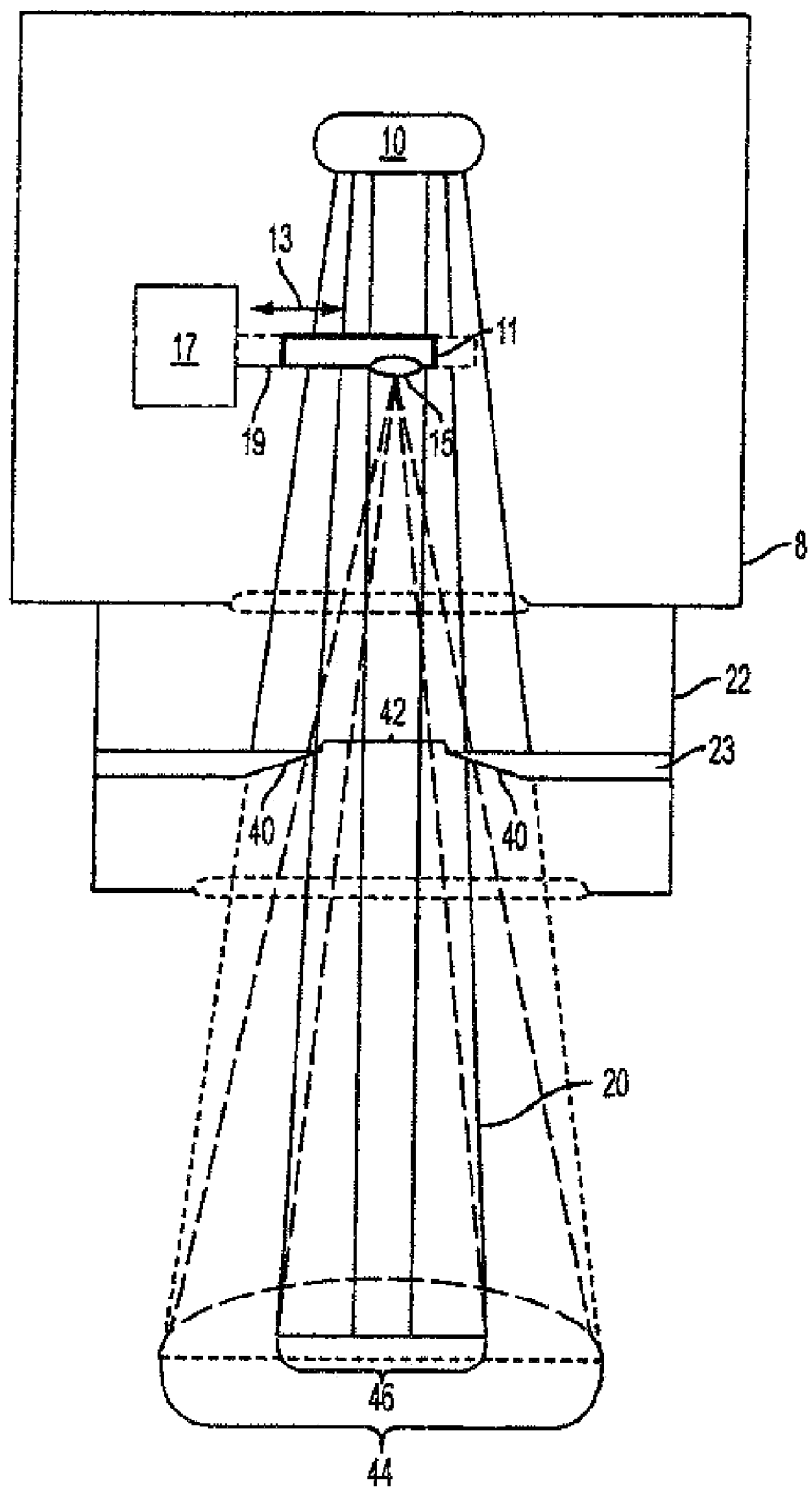
FIG. 2a is a schematic diagram highlighting a camera and focusing assembly that is a modification of the camera and assembly depicted in FIG. 2.

FIG. 2A depicts a modification to the embodiment of the X-ray diagnostic imaging apparatus described in detail with respect to FIGS. 1a and 2. The modification includes substituting a miniature CCD-based camera 11, for camera 12 (of FIGS. 1 and 2), and substituting camera controller 17 for mirror drive assembly 16 (FIGS. 1 and 2). The CCD-based camera 11 essentially includes a focusing lens assembly 15 for focusing light received from the FOV 44, 46 and directing the received light to a CCD imager (neither shown in detail). The CCD-based camera 11 and focusing lens assembly 15 are movably supported by a track 19 to move in and out of the path that is taken by x-ray beam 20 when actively imaging. That is, camera controller 17 responds to the feedback control signal to move the CCD-based camera 11 left-to-right, and back as shown by arrow 13 of FIG. 2A, along track 19. Camera controller 17 receives the feedback control signal from position detecting and control device 18, and communicates camera position information, status, camera image frames, etc., to the image control and processing sub-system 28, through the position detecting and control device 18.

The camera 11 is adjusted to receive light reflected from the FOV through focusing lens assembly 15 during pre-examination testing. To do so, the camera (and therefore the lens assembly) is moved to a position within a cross-sectional area through which the pre-collimated X-ray beam 20 will pass, while the X-ray tube is inactive. The camera 11, track 19, CCD camera assembly 17 operate together to move the camera quickly and with little or minimal detectable mechanical vibration. Hence, imaging could be stopped and the camera moved into position to view the instant collimator-defined FOV, focus and acquire image frames sufficient to generate an image for display, and move out of the beam path in just a few seconds. Any adjustments necessary to the FOV and/or patient positioning is immediately apparent by the camera view without having to perform a visual check at the patient's location. Various CCD-based cameras are available for use in accordance with an embodiment of the present invention, including RL-B914FF miniature camera with a ¼ inch Sony CCD image sensor by Shenzhen Wanjiaan, and TMX10 camera by ADIMEC Advanced Image Systems, to name just two. While just about any known off-the-shelf camera or video system may be used in accordance with an embodiment of the present invention, it may be presumed that an off-the-shelf unit would require some modification for incorporation into and operation with the exemplary embodiments as described.

Figure 3:
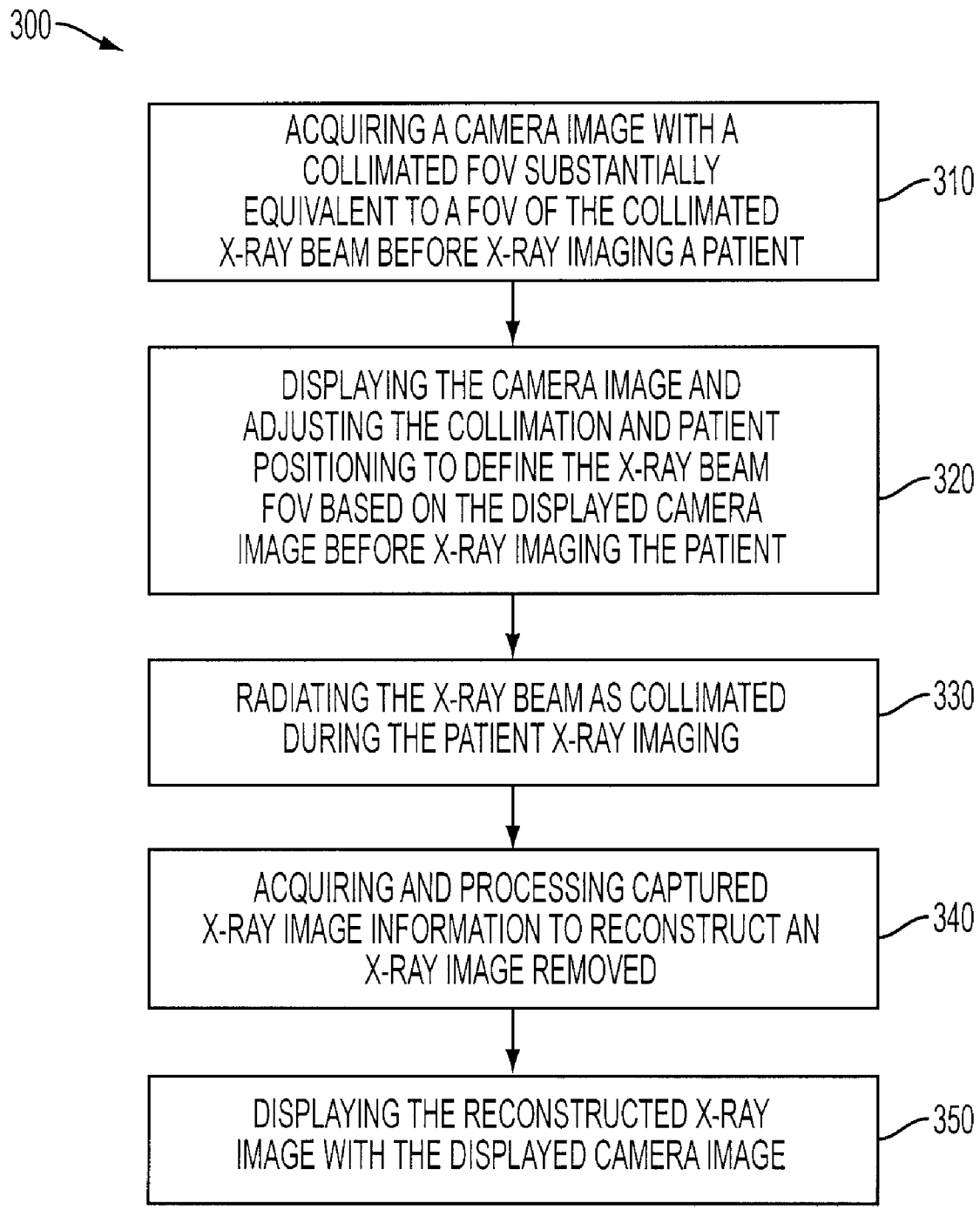
FIG. 3 is a schematic flow diagram that depicts an embodiment of the method for X-ray imaging with the camera for improved imaging in accordance with an embodiment of the present invention.

FIG. 3 depicts a schematic flow diagram of a preferred method 300 for X-ray imaging of the invention. The method 300 allows for X-ray diagnostic imaging using a camera image controlled to image a field of view (FOV) that is substantially coincident and coplanar with a radiation footprint or FOV of an X-ray beam radiated towards to a patient under examination. Both the X-ray beam and camera FOVs are shaped and/or limited by collimation. Block 310 of FIG. 3 represents a step of acquiring a camera image with a collimated FOV substantially equivalent to a FOV of the collimated X-ray beam before X-ray imaging a patient. Block 320 represents a step of displaying the camera image and adjusting the collimation and patient positioning to define the X-ray beam FOV based on the displayed camera image before X-ray imaging the patient. Block 330 represents a step of radiating the X-ray beam as collimated during the patient X-ray imaging. Block 340 represents a step of acquiring and processing captured X-ray image information to reconstruct an X-ray image. Block 350 represents a step of displaying the reconstructed X-ray image with the displayed camera image.

It should be noted that the step of radiating may be postponed or interrupted for X-ray beam readjustment or patient repositioning for desired X-ray imaging based on the camera image displayed. The step of displaying preferably includes displaying the camera image and X-ray image. The step of adjusting is based on a feedback control signal automatically generated in accordance with the camera image, or generated by user input in response to viewing the camera image. The method may be implemented on any known X-ray system, where the steps of radiating, acquiring and processing and displaying are conducted for displaying a live X-ray image, the live X-ray imaging may include subtraction imaging processing, and the subtraction imaging processing may include live fluoroscopic roadmapping. Live fluoroscopic roadmapping may be carried out in accordance with an embodiment of the present invention to support an interventional procedure. The method may further include displaying the X-ray image at a remote location, and in DICOM format.

Although a few examples of the present invention have been shown and described, it should be appreciated by those skilled in the art that changes may be made in these embodiments without departing from the principles and spirit of the invention, the scope of which is defined in the claims and their equivalents.

The invention claimed is:

1. An X-ray diagnostic imaging system, comprising:
    an X-ray source for generating and controlling an X-ray beam radiated towards a patient under examination, the X-ray source comprising an X-ray tube, an X-ray collimator assembly and a camera and camera control apparatus disposed proximate the X-ray tube to image a camera field of view (FOV) that is substantially coincident with a maximum footprint or FOV of the X-ray beam, wherein both the X-ray beam and camera FOVs are shaped and/or limited by collimator assembly operation;
    an X-ray imaging device arranged for receiving the X-ray beam and acquiring latent image frames of a region of interest (ROI) within the patient's anatomy;
    a system controller coupled to the X-ray source and X-ray imaging device for controlling the X-ray tube, X-ray collimator assembly, camera and camera control apparatus, and X-ray imaging device positioning;
    an image processing chain comprising an image processor that is coupled to the system controller, which receives acquired image frames from the X-ray imaging device for processing; and
    a display device coupled to the image processing chain for displaying post-processed image frames as an X-ray diagnostic image of the ROI;
    wherein the camera control apparatus retractably positions the camera into and out of a path of the X-ray beam when the X-ray tube is inactive to focus the camera to image the camera FOV at the patient wherein a feedback signal is generated in response to an image signal acquired by the camera, the feedback signal provided to system to control the collimator assembly and camera operation.

2. The X-ray diagnostic imaging system as set forth in claim 1, wherein the camera control apparatus includes a mirror.

3. The X-ray imaging system as set forth in claim 1, wherein the mirror is retractably positioned by the camera control apparatus within a cross-sectional area of the X-ray beam path to focus the camera to image the camera FOV.

4. The X-ray imaging system as set forth in claim 3, wherein the mirror is operational for camera image acquisition only when the X-ray tube is not radiating.

5. The X-ray diagnostic imaging system as set forth in claim 1, wherein the position of the camera and the X-ray tube is synchronized when a collimator beam-limiting means defines a collimator opening that is at a maximum.

6. The X-ray diagnostic imaging system as set forth in claim 1, wherein the feedback signal is used for automatic synchronization of the camera and X-ray beam FOVs.

7. The X-ray diagnostic imaging system as set forth in claim 1, wherein the camera image is displayed with the X-ray image on the display device during normal imaging operation.

8. The X-ray imaging system as set forth in claim 7, wherein the collimator opening and camera FOV are clearly visualized in the camera image.

9. The X-ray imaging system as set forth in claim 1, wherein the camera is controlled to acquire current images only when the X-ray system is not actively imaging.

10. The X-ray imaging system as set forth in claim 1, wherein a user provides an input to generate the feedback signal in response to viewing a camera image reconstructed from the camera image signal to control the collimator assembly and camera operation.

11. The X-ray imaging system as set forth in claim 1, further comprising a conventional light that lights the FOV.

12. The X-ray imaging system as set forth in claim 1, wherein adjusting a size of the collimator constricts the FOV of the X-ray beam and camera substantially similarly.

13. The X-ray imaging system as set forth in claim 1, wherein the camera is a video camera.

14. The X-ray imaging system as set forth in claim 1, wherein the camera, focusing assembly and mirror are maintained outside a maximum cross-section area of the X-ray beam path with the X-ray tube positioned at a maximum distance from the imaging device.

15. The X-ray imaging system as set forth in claim 1, where the camera is arranged with the X-ray tube in a closed housing that allows for imaging.

16. The X-ray diagnostic imaging system as set forth in claim 1, wherein the X-ray source and X-ray imaging device are disposed at opposite ends of a C-ram constructed to rotate about the patient in a substantially circular path, and wherein the X-ray imaging device comprises a digital detector.

17. The X-ray diagnostic imaging system as set forth in claim 16, wherein the C-ram X-ray system is limited in mobility to image a top hemisphere of a plane that is substantially coplanar with a fixed plane of the detector.

18. The X-ray diagnostic imaging system as set forth in claim 1, wherein the X-ray system is constructed to conduct interventional imaging, and wherein the X-ray imaging device comprises a digital detector.

19. The X-ray diagnostic imaging system as set forth in claim 18, wherein the X-ray system is constructed to conduct X-ray fluoroscopic imaging.

20. The X-ray diagnostic imaging system as set forth in claim 19, wherein the X-ray system is constructed to conduct live Roadmapping.

21. The X-ray diagnostic imaging system as set forth in claim 19, further comprising an image contrast injector and contrast injector control mechanism coupled to the system controller and controllable via a user interface.

22. The X-ray imaging system as set forth in claim 1, wherein the X-ray imaging device comprises an X-ray image intensifier assembly and the system controller includes image intensifier processing and control means.

23. The X-ray imaging system as set forth in claim 1, wherein the X-ray imaging device comprises an X-ray film cartridge, and the system controller and image processing chain are constructed to conduct X-ray film imaging.

24. The X-ray diagnostic imaging system as set forth in claim 1, further comprising a user workstation.

25. The X-ray diagnostic imaging system as set forth in claim 1, further comprising a hard disk or other direct memory device for storing the X-ray diagnostic images and/or camera images.

26. The X-ray diagnostic imaging system as set forth in claim 1, wherein the X-ray diagnostic image is arranged in DICOM format.

27. The X-ray diagnostic imaging system as set forth in claim 1, further comprising a user interface, wherein the user interface comprises without limitation one of a keyboard, a trackball device, joystick, mouse, touch pad, light pen, eye sensor.

28. The X-ray diagnostic imaging system as set forth in claim 1, further comprising a patient-support table with table control means in electrical communication with the system controller, wherein the X-ray source is mounted above the table such that a user may control table, X-ray imaging device and patient position via a user interface to affect FOV.

29. The X-ray diagnostic imaging system as set forth in claim 1, further comprising a patient-support table with table control means in electrical communication with the system controller, wherein the X-ray source is mounted below the table such that a user may control table, X-ray imaging device and patient position via a user interface to affect FOV.

30. The X-ray diagnostic imaging system as set forth in claim 1, further comprising a console in communication with the X-ray system, which console includes a display and user interface by which a user may conduct imaging operations at a fixed distance from the system.

31. An X-ray diagnostic imaging system, comprising:
   an X-ray source for generating and controlling an X-ray beam radiated towards a patient under examination, the X-ray source comprising an X-ray tube, an X-ray collimator assembly and a miniaturized CCD-based camera with lens and camera control apparatus disposed proximate the X-ray tube to image a camera field of view (FOV) that is substantially coincident with a maximum footprint or FOV of the X-ray beam when the X-ray tube is inactive, wherein both the X-ray beam and camera FOVs are shaped and/or limited by collimator assembly operation;
   an X-ray imaging device arranged for receiving the X-ray beam and acquiring latent image frames of a region of interest (ROI) within the patient's anatomy when the X-ray tube is active;
   a system controller coupled to the X-ray source and X-ray imaging device for controlling the X-ray tube, X-ray collimator assembly, CCD-based camera with lens and camera control apparatus, and X-ray imaging device positioning;
   an image processing chain comprising an image processor that is coupled to the system controller, which receives acquired image frames from the X-ray imaging device for processing; and
   a display device coupled to the image processing chain for displaying post-processed image frames as an X-ray diagnostic image of the ROI;
   wherein during inactive X-ray imaging operation, the camera control apparatus retractably positions one of the CCD camera and lens into and out of an X-ray beam path in order to image the camera FOV at the patient; and
   wherein a feedback signal is generated in response to processing the camera FOV image to control collimator assembly, camera and camera control apparatus operation.

32. A method for X-ray diagnostic imaging that includes using a camera and retractable mirror to image a camera field of view (FOV) that is substantially coincident and coplanar with a radiation footprint or FOV of an X-ray beam radiated towards a patient under examination, wherein both the X-ray beam and camera FOVs are shaped and/or limited by collimation, the method comprising the steps of:
   acquiring a camera image of the camera FOV that is equivalent to the X-ray beam FOV by retractable positioning one of the camera and retractable mirror into a path traversed by the X-ray beam to capture the camera FOV before actively X-ray imaging the patient;
   displaying the camera image;
   adjusting collimation and patient positioning to define the X-ray beam FOV based on the displayed camera image, before actively X-ray imaging the patient;
   radiating the collimated X-ray beam towards the patient during active X-ray imaging;
   acquiring and processing X-ray image information to reconstruct an X-ray image from the acquired X-ray image information; and
   displaying the reconstructed X-ray image with the displayed camera image.

33. The method of X-ray imaging as set forth in claim 32, wherein the step of radiating may be postponed or interrupted for X-ray beam readjustment or patient repositioning for desired X-ray imaging based on the camera image displayed.

34. The method for X-ray diagnostic imaging as set forth in claim 32, wherein the camera image and X-ray image are displayed together.

35. The method for X-ray diagnostic imaging as set forth in claim 32, wherein the step of adjusting is based on a feedback control signal automatically generated in accordance with the camera image.

36. The method for X-ray diagnostic imaging as set forth in claim 32, wherein the step of adjusting is based on a feedback control signal generated by user input in response to viewing the camera image.

37. The method for X-ray imaging as set forth in claim 32, wherein the steps of radiating, acquiring and processing and displaying are conducted for displaying a live X-ray image.

38. The method for X-ray imaging as set forth in claim 37, further comprising a step of subtraction imaging processing.

39. The method for X-ray imaging as set forth in claim 38, wherein the step of subtraction imaging is carried out during a live fluoroscopic roadmapping process.

40. The method for X-ray imaging as set forth in claim 39, wherein the live fluoroscopic roadmapping is carried out to support an interventional procedure.

41. The method for X-ray imaging as set forth in claim 32, wherein the step of displaying includes displaying the X-ray image at a remote location.

42. The method for X-ray imaging as set forth in claim 32, wherein the step of acquiring and processing includes storing the live X-ray image in DICOM format.

43. A program storage device readable by machine, tangibly embodying a program of instructions executable by the machine comprising an X-ray imaging system to perform the method steps set forth in claim 32.

* * * * *